United States Patent
Nicholls

(10) Patent No.: US 8,172,867 B2
(45) Date of Patent: May 8, 2012

(54) SKIN PRICKING DEVICE

(75) Inventor: Clive Nicholls, Stokenchurch (GB)

(73) Assignee: Owen Mumford Limited, Woodstock, Oxon (GB)

(*) Notice: Subject to any disclaimer, the term of this patent is extended or adjusted under 35 U.S.C. 154(b) by 353 days.

(21) Appl. No.: 12/373,915

(22) PCT Filed: Jun. 11, 2007

(86) PCT No.: PCT/GB2007/050330
§ 371 (c)(1),
(2), (4) Date: Apr. 22, 2009

(87) PCT Pub. No.: WO2008/009985
PCT Pub. Date: Jan. 24, 2008

(65) Prior Publication Data
US 2009/0287237 A1  Nov. 19, 2009

(30) Foreign Application Priority Data
Jul. 18, 2006 (GB) .................. 0614233.5

(51) Int. Cl.
*A61B 17/32* (2006.01)
(52) U.S. Cl. ...................................... 606/182
(58) Field of Classification Search .......... 606/181, 606/182, 183; 604/136, 130; 600/573, 578, 600/583, 584
See application file for complete search history.

(56) References Cited

U.S. PATENT DOCUMENTS

| | | | | |
|---|---|---|---|---|
| 4,817,603 A * | 4/1989 | Turner et al. | ........ | 606/182 |
| 4,869,249 A * | 9/1989 | Crossman et al. | ........ | 606/182 |
| 5,026,388 A * | 6/1991 | Ingalz | ........ | 606/182 |
| 5,350,392 A * | 9/1994 | Purcell et al. | ........ | 606/182 |
| 5,366,470 A * | 11/1994 | Ramel | ........ | 606/183 |
| 5,540,709 A * | 7/1996 | Ramel | ........ | 606/183 |
| 6,306,152 B1 * | 10/2001 | Verdonk et al. | ........ | 606/182 |
| 6,432,120 B1 * | 8/2002 | Teo | ........ | 606/182 |
| 6,852,119 B1 * | 2/2005 | Abulhaj et al. | ........ | 606/182 |
| 2002/0087180 A1 * | 7/2002 | Searle et al. | ........ | 606/181 |
| 2003/0216767 A1 * | 11/2003 | List et al. | ........ | 606/181 |
| 2004/0260325 A1 | 12/2004 | Kuhr et al. | | |
| 2005/0085840 A1 | 4/2005 | Yi et al. | | |
| 2005/0261716 A1 * | 11/2005 | Sakata et al. | ........ | 606/181 |
| 2006/0008389 A1 * | 1/2006 | Sacherer et al. | ........ | 422/102 |

OTHER PUBLICATIONS

International Search Report dated Sep. 19, 2007, from corresponding PCT application.

* cited by examiner

*Primary Examiner* — S. Thomas Hughes
*Assistant Examiner* — David Eastwood
(74) *Attorney, Agent, or Firm* — Young & Thompson

(57) ABSTRACT

A skin pricking device includes first (12) and second (14) housing parts telescopically coupled together. A lancet (26) and a firing mechanism (32,38) are disposed within the first housing part, whilst a membrane (25) is disposed over an open end of the first housing part to seal the first housing part containing the lancet and the firing mechanism. Movement of the second housing part towards the first housing part activates the firing mechanism thereby driving a tip (30) of the lancet through the membrane and through an opening (18) in the second housing part.

20 Claims, 5 Drawing Sheets

SKIN PRICKING DEVICE

The present invention relates to a skin pricking device and in particular, though not necessarily, to a skin pricking device for use in providing a sample of blood.

In the medical and related diagnostic and testing fields, it is often required to take small samples of blood from a subject for the purpose of testing or analysing the blood. A common way of achieving this is by using a small needle to pierce the skin at a location where blood vessels are close to the surface. The combination of a needle and its holder is commonly known as a lancet. In order to avoid infection and contamination, lancets are preferably intended for single use and are disposable. They must therefore be compact to allow users to carry multiple lancets on their person, and cheap to manufacture.

A number of disposable lancet devices are currently on the market. These include the Unistik™ manufactured and marketed by Owen Mumford Ltd (Woodstock, UK). The current designs comprise a moulded plastics casing within which is mounted a short, spring-loaded needle. A trigger is formed in the casing which, when depressed, releases the lancet causing the tip to be fired out through an opening in the casing. Some of the current designs require an operator to preload or cock the spring prior to firing. In other designs, the lancet devices are supplied already cocked. It is also generally necessary for users to remove a cap from the front of the device or the needle tip prior to firing. Users must therefore perform at least two steps, and sometimes three, in order to perform the blood sampling procedure.

There exists a desire for a lancet device which is simpler to operate than current designs. Of course, any improved design must meet high standards with regard to manufacturing costs. It must also be reliable, ensuring that lancet devices are provided to users in an operable condition. The present invention has been devised with the foregoing in mind.

According to the present invention there is provided a skin pricking device comprising:
first and second housing parts telescopically coupled together;
a lancet and a firing mechanism disposed within the first housing part; and
a membrane disposed over an open end of the first housing part to seal the first housing part containing said lancet and said firing mechanism
wherein movement of said second housing part towards said first housing part activates said firing mechanism thereby driving a tip of the lancet through said membrane and through an opening in said second housing part.

It is an advantage that the device is easy to use, and that it can be used with one hand. The majority of the components of the device (including the needle) can be manufactured from plastics materials, providing the advantage that it is inexpensive and easy to manufacture. Using a membrane provides the further advantage that the needle can simply pierce through it, rather than needing a separate cap that as to be removed before the device can be used. Furthermore, the whole of the interior of the first housing part is sealed and remains sterile until the device is fired.

In an embodiment, the second housing part has an external contact surface for contacting skin to be pricked. The firing mechanism may be configured to be actuated by pushing the first housing part towards the second housing part and the skin to be pricked.

Preferably the firing mechanism comprises a biasing means. More preferably, the biasing means is coupled to an inner surface of the first housing parts and to the lancet. The biasing means may be a spring. In a preferred embodiment, the biasing means is a helical spring.

The device of any preceding claim, the second housing part being provided with one or more formations which penetrate said membrane when the first and second housing parts are moved together, the formations thereafter activating said firing mechanism.

According to a preferred embodiment of the invention, the device comprises locking means provided on an inner surface of said first housing for engaging with said lancet to retain the lancet against the action of said biasing means, said formation(s) on the second part being arranged to engage with said locking means following penetration of the membrane to release the lancet Said locking means may comprise one or more spreadable fingers.

The biasing means may be configured to retract the needle fully into the housing after the needle has been driven through the opening. This advantageously prevents accidental pricking after use.

Preferably, the first and second housing parts comprise complementary engageable formations for resisting their relative movement prior to and/or after actuation of the device. The first housing part may be mounted telescopically within the second housing part and may comprise one or more flanges on its outer surface. The second housing part may comprise one or more flanges configured to engage with the one or more flanges of the first housing part prior to and/or after actuation of the device.

In an embodiment, the second housing part flexes on actuation of the device to allow the first housing part to move telescopically within it.

The second housing part may comprise apertures in the surface that is brought into contact with the skin, and the device may further comprise one or more snap-fit components that can pass through the apertures after the device has been actuated, to secure the device from further actuation after use. This provides the advantage that it is evident that a device has already been used and should be discarded. This helps avoid risks of contamination and infection.

For a better understanding of the present invention and in order to show how the same may be carried into effect, reference will now be made by way of example to the accompanying drawings in which.

The Figures illustrate a skin pricking device designed for pricking a person's skin to, for example, provide a small blood sample. Typically the device is used to prick the pad of a person's finger, leaving a small spot of blood on the finger. This spot can then be collected, e.g. using a test strip, for use in performing a measurement or test. The device is shown in FIGS. 1 and 2 in the "ready-to-use" or "starting" position, prior to actuation of the device.

Figure 1:
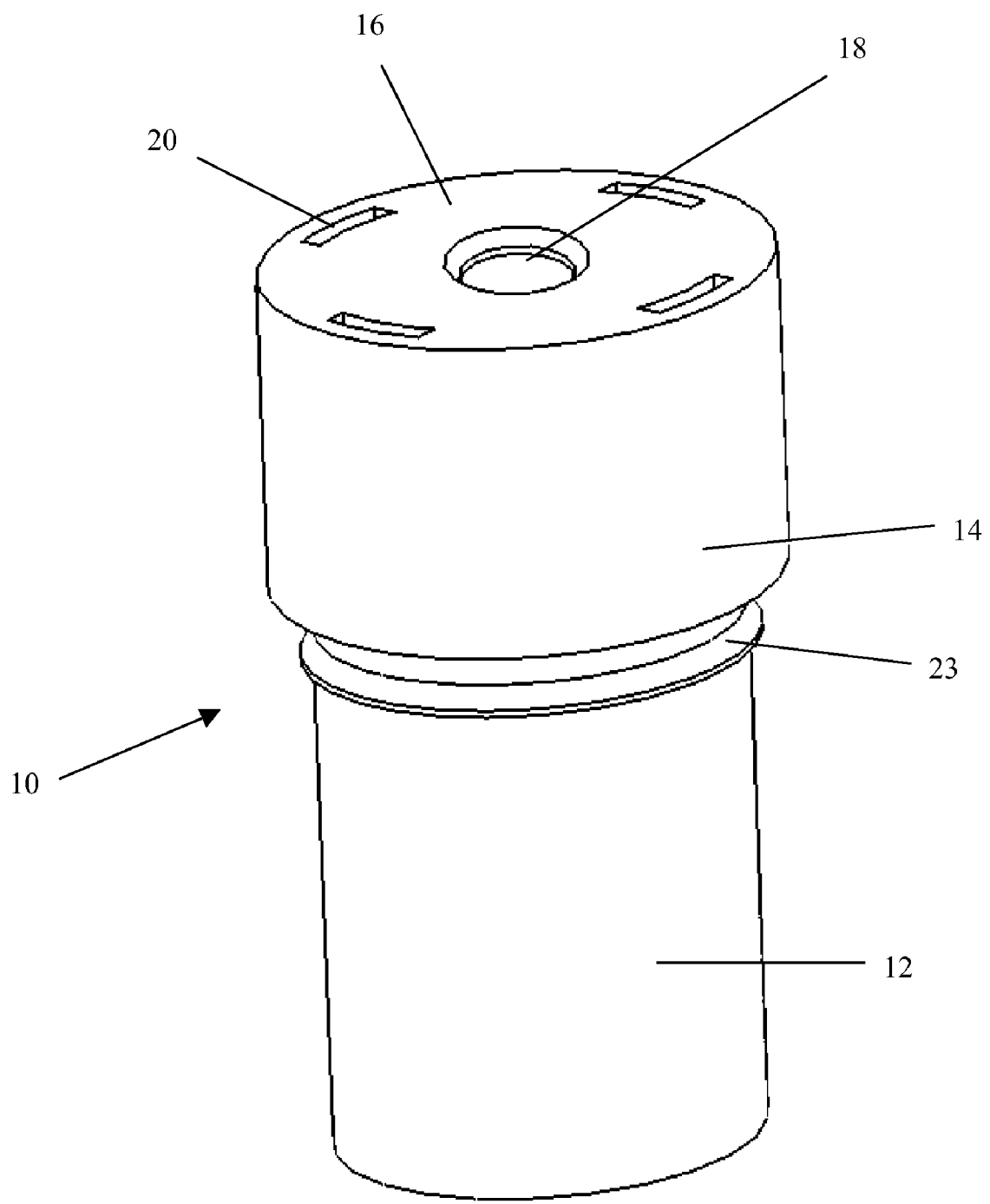
FIG. 1 is a perspective view of a skin pricking device.

Referring to FIG. 1, a skin pricking device 10 has a lower housing part 12 and an upper housing part 14. The references to "lower" and "upper" have been chosen for convenience, and refer to the embodiment in the orientation as shown in FIGS. 1 to 4. The housing parts 12, 14 are circular or elliptical in cross-section. The housing parts 12, 14 are each open at one end, and the lower housing part 12 is mounted telescopically within the upper housing part 14, with their open ends facing each other to form a cavity inside the device 10. The closed end of the upper housing part 14 comprises a flat surface 16, with an aperture 18 located at the centre thereof. Apertures 20 are also provided around the periphery of the upper surface 16. In the embodiment shown, four apertures 20 are provided, but embodiments with any number of apertures, including a single aperture, are envisaged. An annular flange or projection 23 is provided around the outer surface of the lower housing part 14, located towards the open end thereof.

Figure 2:
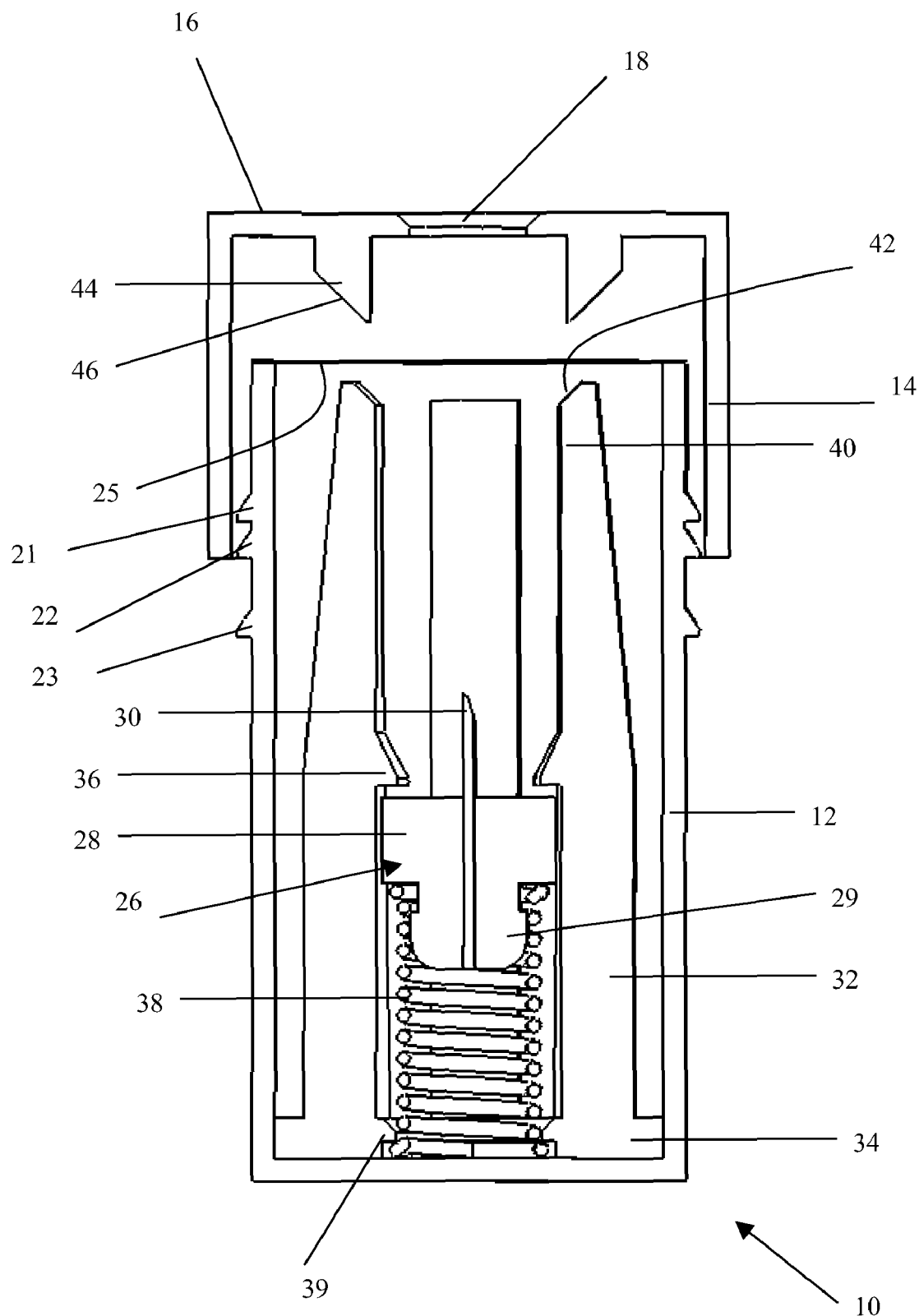
FIG. 2 is a cross-section through the skin pricking device of FIG. 1 in a vertical plane.
Figure 5:
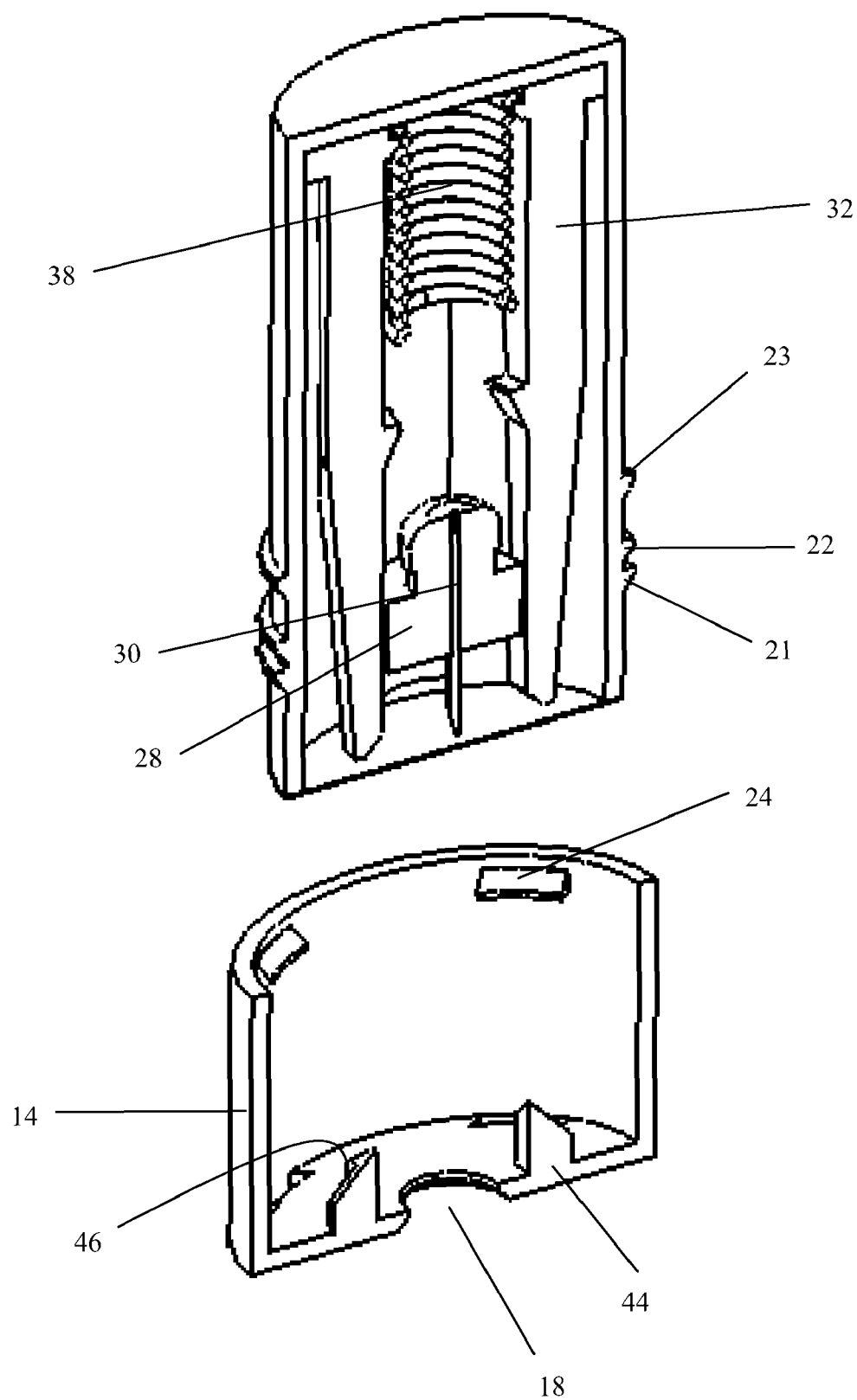
FIG. 5 is a exploded cross-sectional view (at 180° to the device in FIGS. 1 to 4) through the skin pricking device after use.

Referring to FIG. 2, the flange 23 can be seen, and two additional flanges or projections 22, 23 are provided around the outer surface of the lower housing part 12. The flanges 21, 22, 23 have wedge-like profiles, tapering from their lower edge upwards. The upper housing part 14 also has a flange or projection 24, located towards the open end thereof. Referring briefly to FIG. 5, the flange 24 comprises a series of wedge-shaped projections spaced around the interior surface of the upper housing part 14 towards the open end thereof. The wedged flanges 24 taper towards the open end of the upper housing part 14. Referring again to FIG. 2, a membrane 25 is provided, spanning the open upper end of the lower housing part 12. The membrane 25 may be fabricated from a number of different materials, including a metallic foil (e.g. aluminium), a plastic film, paper, rubber, or thermoplastic elastomer (TPE).

A lancet 26 is provided within the lower housing part 12. The lancet 26 comprises a lancet body 28, and a needle 30 embedded within the lancet body 28. The lateral dimensions of the upper part of the lancet body 28 are greater than those of the lower part 29 of the lancet body 28. A tip of the needle 30 points vertically upwardly, towards the opening 18.

The lancet 26 is held in the starting position by a lancet retaining means 32. A base 34 of the retainer 32 is fixed to the inner base of the lower housing part 12. Inwardly extending projections 36 overlap the upper surface of the lancet body 28, holding it in an armed position. The needle 30 is disposed between the projections 36.

The lancet body 28 is urged upwardly into abutment with the projections 36 with a biasing means. In the embodiment shown, the biasing means is a coiled helical spring 38, which is pre-loaded (i.e. under compression). A first end of the spring 38 is held in contact with the base of the lower housing part 12 by inwardly projecting retainers 39. The other end of the spring 38 is coiled around the lower part 29 of the lancet body 28.

In the embodiment shown in FIG. 2, the retainer 32 comprises upwardly extending arms. The retainer projections 36 are located about half way up the height of the retainer arms 32. The retainer arms 32 narrow slightly towards their upper extremities. The tips 40 of the arms 32 are angled inwardly, to provide a contact surface 42.

The upper housing part 14 comprises downwardly extending projections, or teeth 44. The teeth 44 are angled to provide contact surfaces 46. The teeth 44 are located generally above the tips 40 of the retainer arms 32, and each contact surface 42 of the retainer arms is angled in the same direction as the respective contact surface 46 of the teeth 44 located above it. The teeth 44 are configured to engage and partially surround the tips 40 of the retainer arms 32, as shown in FIG. 5.

Figure 3:
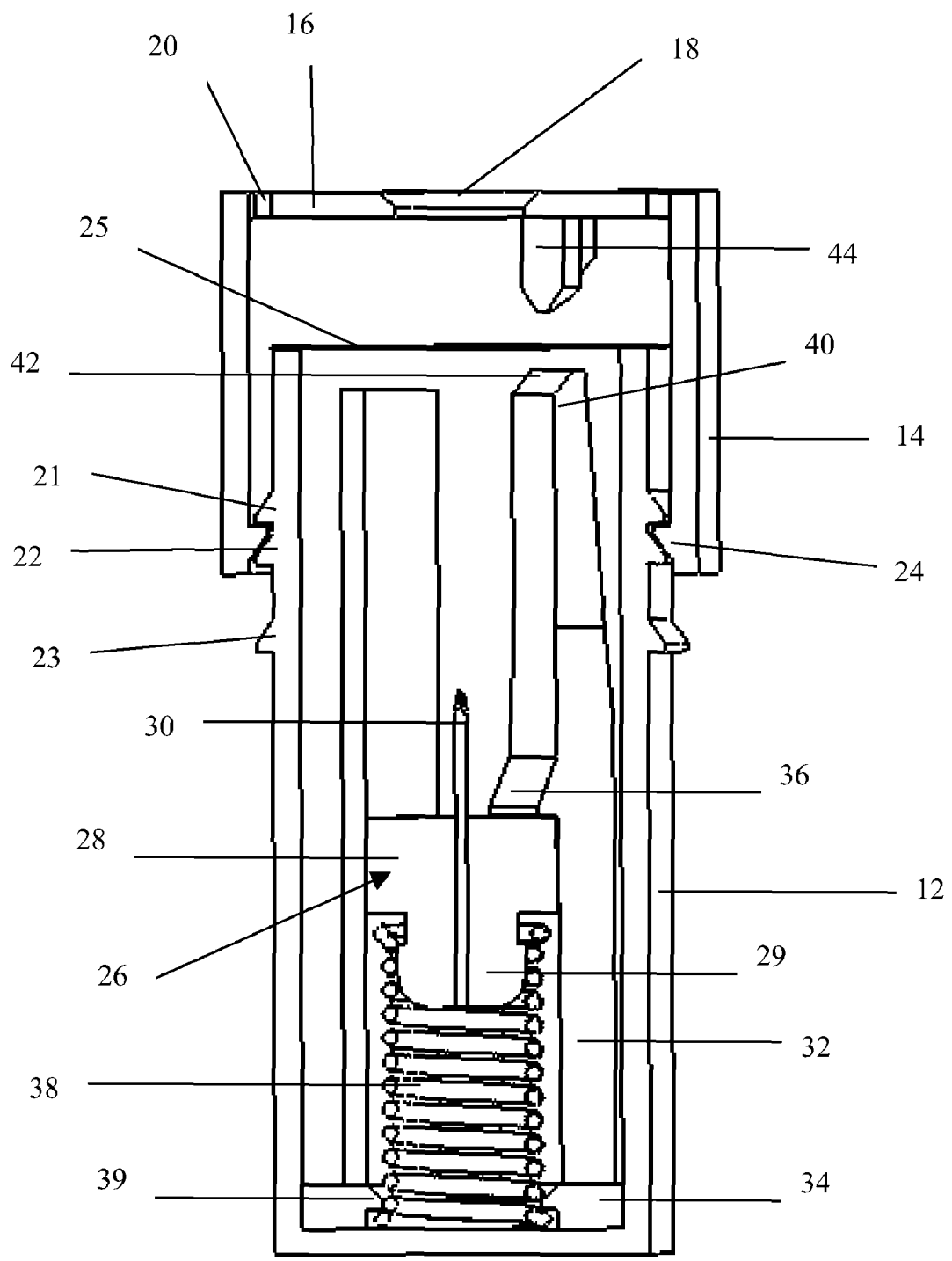
FIG. 3 is a cross-section through the skin pricking device in a starting position at 45° to the view of FIG. 2.
Figure 4:
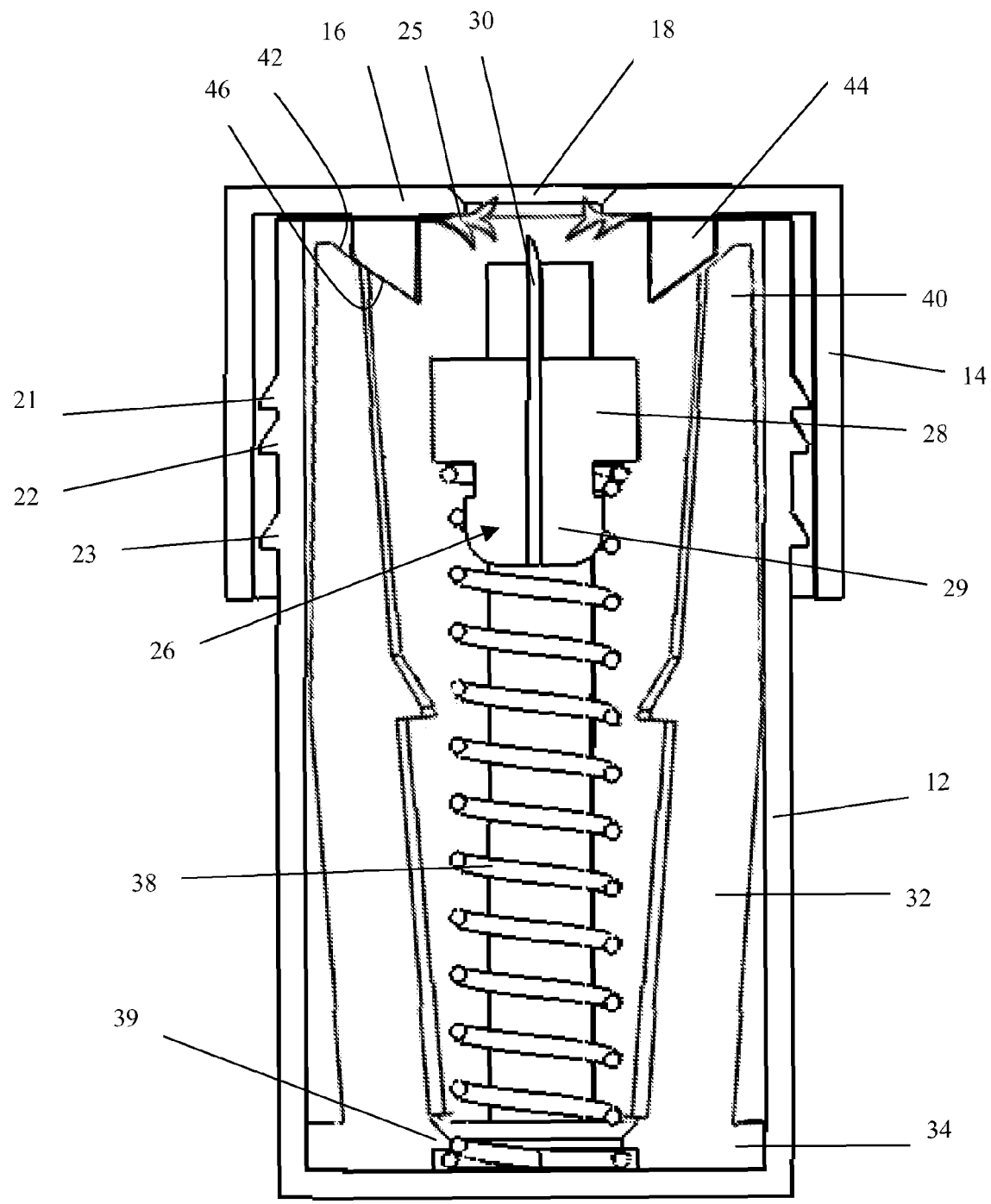
FIG. 4 is a cross-section through the skin pricking device shown after use in the vertical plane of FIG. 2.

Referring now to FIG. 3, the skin pricking device 10 is shown again in the starting position, with the lancet 26 is held in position by a lancet retaining means 32. The flange 24 of the upper housing part 14 is located between the two uppermost flanges 21, 22 of the lower housing part 12 to restrict axial movement, and prevent separation, of the two housing parts 12, 14. FIG. 4 shows the skin pricking device 10 after use, where the flat surface of the lowermost flange 23 of the lower housing part 12 abuts the flat surface of the flange 24 of the upper housing part 14, to prevent separation of the lower and upper housing parts 12, 14. FIG. 5 also shows the device 10 after use, after the spring 38 has returned to its position against the base of the lower housing part 12.

In the starting position of the device 10 (shown in FIGS. 2 and 3), the flanges 24 of the upper housing part 14 are held between the flanges 21, 22 of the lower housing part 12. In use, an operator holds the flat upper surface 16 of the upper housing part 14 against their own, or another person's, skin that is to be pricked. The operator then pushes the lower housing part 12 into the upper housing part 14, the flange 24 of the upper housing part 14 flexing over the tapered flanges 22, 23. The membrane 25 is thus conveyed towards the teeth 44, which pierce the membrane 25 on contact therewith. The pierced membrane 25 is shown in FIG. 4. Continued advancement of the lower housing part 12 into the upper housing part 14 brings the teeth 44 into contact with the tips 40 of the retainer arms 32 (as shown in FIG. 4). The angled surfaces 46 of the teeth 44 push the retainer arms 32 outward on contact with the angled surfaces 42 of the tips 40 of the retainer arms 32. This outward movement of the retainer arms 32 continues until the retainer projections 36 have been sufficiently displaced laterally to release the lancet 26. The spring 38 then rapidly expands, releasing the energy hitherto fore stored therein. This drives the needle 30 through the lower housing part 12, through the membrane 25 and through the opening 18 in the upper housing part 14 to prick the skin of the person. Since the upper part of the lancet body 28 is larger than the diameter of the aperture 18, only the needle 30 can protrude through the opening 18. The length of the needle 32 can therefore be chosen such that it will penetrate a person's skin at a predetermined depth. It is to be noted that the separation of the teeth 44 is sufficient to allow the lancet body to travel between them (as shown in FIG. 5).

At this point, after actuation of the device and when the upper surface of the lancet body has contacted the surface of the first housing surrounding the opening 18, the spring is overextended. The spring 38 retracts to pull the needle 32 back through the aperture 18, and back into the housing 12, 14 (as shown in FIG. 5). There will subsequently be insufficient energy within the spring to urge the needle 30 back out of the aperture 18, and so the needle 32 is thereby secured within the housing 12, 14 after use. This prevents any skin pricking accidents being caused by the needle 22.

After use, the flat surface of the lowermost flange 23 of the lower housing part 12 abuts the flat surface of the flange 24 of the upper housing part 14, which ensures that the device is "locked down" after firing. This provides a clear indication that the device has already been used.

The whole device 10 is sterilized once assembled. The membrane 25 also ensures that the sterility is maintained until the device 10 is used.

The device 10 is very simple to use, and can be operated with one hand. The operator need only hold the lower housing part 12 and, with the upper surface 16 of the upper housing part 14 in position for pricking the skin, simply push the lower housing part 12 towards the skin.

It will be appreciated by those skilled in the art that various modifications may be made to the above described embodiment without departing from the scope of the present invention.

The invention claimed is:

1. A skin pricking device comprising:
   first and second housing parts telescopically coupled together;
   a lancet and a firing mechanism disposed within the first housing part; and
   a membrane disposed over an open end of the first housing part to seal the first housing part containing said lancet and said firing mechanism wherein movement of said second housing part towards said first housing part activates said firing mechanism thereby driving a tip of the lancet through said membrane and through an opening in said second housing part.

2. The device of claim 1, wherein the firing mechanism comprises a biasing means.

3. The device of claim 2, wherein the biasing means is coupled to an inner surface of the first housing part and to the lancet.

4. The device of claim 2, wherein the biasing means is a spring.

5. The device of claim 2, wherein the biasing means is a helical spring.

6. The device of claim 2, wherein the biasing means is configured to retract the needle fully into the housing after the needle has been driven through the opening.

7. The device of claim 1, further comprising lancet retaining means for retaining the lancet within the first housing part prior to actuation of the firing mechanism.

8. The device of claim 1, wherein the second housing part has an external contact surface for contacting skin to be pricked.

9. The device of claim 2, the second housing part being provided with one or more formations which penetrate said membrane when the first and
   second housing parts are moved together, the formations thereafter activating said firing mechanism.

10. The device of claim 9, comprising locking means provided on an inner surface of said first housing for engaging with said lancet to retain the lancet against the action of said biasing means, said formation(s) on the second housing part being arranged to engage with said locking means following penetration of the membrane to release the lancet.

11. The device of claim 10, said locking means comprising one or more spreadable fingers.

12. The device of claim 1, wherein the first and second housing parts comprise complementary engageable formations for resisting their relative movement prior to and/or after actuation of the device.

13. The device of claim 12, wherein the first housing part is mounted telescopically within the second housing part and comprises one or more flanges on its outer surface, and the second housing part comprises one or more flanges configured to engage with the one or more flanges of the first housing part prior to and/or after actuation of the device.

14. The device of claim 13, wherein the second housing part flexes on actuation of the device to allow the first housing part to move telescopically within it.

15. The device of claim 3, wherein the biasing means is a spring.

16. The device of claim 3, wherein the biasing means is configured to retract the needle fully into the housing after the needle has been driven through the opening.

17. The device of claim 4, wherein the biasing means is configured to retract the needle fully into the housing after the needle has been driven through the opening.

18. The device of claim 5, wherein the biasing means is configured to retract the needle fully into the housing after the needle has been driven through the opening.

19. The device of claim 2, further comprising lancet retaining means for retaining the lancet within the first housing part prior to actuation of the firing mechanism.

20. The device of claim 3, further comprising lancet retaining means for retaining the lancet within the first housing part prior to actuation of the firing mechanism.

* * * * *